United States Patent
Palahnuk et al.

(10) Patent No.: US 6,830,590 B1
(45) Date of Patent: Dec. 14, 2004

(54) LIP ENHANCER

(76) Inventors: Nicholas Palahnuk, 4116 W. Woodland Ave., Burbank, CA (US) 91505; Simon Holden, 8822 Woodrow Wilson Dr., Los Angeles, CA (US) 90068

( * ) Notice: Subject to any disclaimer, the term of this patent is extended or adjusted under 35 U.S.C. 154(b) by 317 days.

(21) Appl. No.: 10/017,579

(22) Filed: Dec. 7, 2001

(51) Int. Cl.[7] .............................. A61F 2/02; A61F 5/56; A61C 5/00; A61C 5/14

(52) U.S. Cl. ................. 623/23.72; 623/11.11; 623/66.1; 128/848; 128/859; 433/136; 433/140; 606/234

(58) Field of Search .............................. 623/11.11, 66.1, 623/23.72, 23.73, 23.74, 902; 128/848, 859; 433/136, 140; 606/234

(56) References Cited

U.S. PATENT DOCUMENTS

| | | | | |
|---|---|---|---|---|
| 3,286,576 A | * | 11/1966 | Alvy ........................... 84/466 |
| 4,338,928 A | * | 7/1982 | Martin et al. ................ 128/857 |
| 5,152,300 A | * | 10/1992 | Horst ........................... 128/857 |
| 5,462,067 A | * | 10/1995 | Shapiro ....................... 128/861 |
| 6,003,515 A | * | 12/1999 | Maness ....................... 128/857 |
| 6,318,370 B1 | * | 11/2001 | Sempere et al. ............ 128/857 |
| 6,328,756 B1 | * | 12/2001 | Amernick .............. 606/204.15 |
| 6,652,275 B2 | * | 11/2003 | Byers ......................... 433/140 |

* cited by examiner

*Primary Examiner*—David H. Willse
*Assistant Examiner*—Javier G. Blanco
(74) *Attorney, Agent, or Firm*—Marshall E. Rosenberg

(57) ABSTRACT

A method and apparatus for enhancing the size of lips. The apparatus is a clear or flesh colored polymer strip with a strong moisture activated adhesive on one side. A user inserts the apparatus on the inside of their lip with an attached applicator. Once in proper position, the user simply pulls the applicator away. When in place the lip enhancer maintains a stretch in the inner lip tissue, causing more of the lip to be exposed externally, thus making the lip appear noticeably larger. Users may talk, eat, and drink while using the lip enhancer.

15 Claims, 2 Drawing Sheets

LIP ENHANCER

FIELD OF THE INVENTION

The present invention relates generally to a lip enhancement apparatus and method, more particularly to a mechanism and method for enhancing the appearance of the lips without use of an injection or plastic surgery.

BACKGROUND OF THE INVENTION

In recent years it has become fashionable for people, particularly actresses, to have fuller looking lips. The most common way in which fuller looking lips are attained is through a lip augmentation procedure, and often through the use of collagen Collagen is a natural structural protein complex found in all mammals. The structure of collagen is complex, but very similar in humans and higher animals, including cattle and pigs. The purified sterile Injectable Collagen used in Cosmetic Plastic Surgery is extracted from cow hides (bovine collagen) and packaged in convenient small quantity syringes. The Injectable Collagen matrix is useful as a filler to build up skin depressions associated with wrinkles, and also as a non-permanent soft tissue augmentation material to highlight the lips, etc.

Because the structure of this bovine collagen is slightly different from human collagen, skin testing of a small quantity is necessary at least one month prior to formal collagen injection treatment to avoid the risk of an allergic reaction. Because the injected Collagen is not exactly the same as native human collagen, the immune system will gradually digest it, preventing permanent incorporation. The Injected Collagen may last for over a year, but in some individuals will only last for several months.

For lips in particular, Collagen treatment is recommended as a preliminary before considering placement of a permanent augmentation material such as Gore-tex strands, Alloderm, or MicroDroplet Fat Injections. Patients who would like a fuller appearance to their lips but are unsure of the permanent results will usually try the collagen replacement therapy first. After liking the fullness created they will have the option of a more permanent procedure such as the Alloderm placement.

Alloderm is highly processed human skin (dermis) that can be grafted or implanted into the upper or lower lip to give your lips a fuller appearance. The treatment with collagen is highly individual. The same amount of collagen that would give fall correction for one person may not be a sufficient amount for another person. Usually, a 1 cc syringe of collagen is used to give adequate correction to the area of concern.

The known risks associated with Collagen Replacement Therapy can be classified into two categories: those associated with the collagen material itself, and those associated with the injection procedure.

The primary known risk of the collagen material is an allergic reaction. About 3% of the population is allergic to bovine collagen. A skin test is done before treatment to help determine whether the patient is allergic to the material. Some physicians will perform the skin test more than once. If the patient is allergic to injectable collagen, treatment should not be done. About 1% to 2% of patients treated will experience an allergic reaction, despite a negative skin test or tests.

This allergic reaction can result in prolonged redness, swelling, firmness and itching or, in rare instances, in formation of an abscess (cyst) that may result in hardness or a scar. These reactions are temporary in nature; however, in a few cases, periodic flare-ups have occurred for more than 24 months.

The primary risk from the injection procedure is bruising and swelling at the injection site. In rare cases, necrosis (tissue sloughing, or shedding, and resulting scab or sear formation) at the injection site may occur.

Some physicians have reported the occurrence of connective tissue diseases such as rheumatoid arthritis, systemic lupus erythematosus, dermatomyositis (DM), and polymyositis (PM) subsequent to collagen injections, in patients with no previous history of these disorders. A comparison of the observed number of cases of PM/DM in the collagen treated population with an estimate of the expected number of cases suggests an association between collagen injections and PM/DM; i.e., there appears to be a higher than expected incidence of PM/DM in the collagen treated population. However, a causal relationship between collagen injection and the onset of autoimmune disease or systemic connective tissue disease has not been established.

While these risks do not manifest themselves in every patient, many prospective patients choose to not undergo lip augmentation procedures because of fears. Because of these fears, these risks, and the time involved with undergoing lip augmentation procedures, there exists a need for a faster, easier, and less dangerous way of augmenting lips.

SUMMARY OF THE INVENTION

The present invention addresses the foregoing needs by providing an inexpensive system for lip augmentation that is extremely easy to use. The lip enhancer is non-surgical, uses no drugs and can be applied in seconds. It is a clear or flesh colored polymer strip with a strong moisture activated adhesive on one side. A user inserts the lip enhancer between their teeth and their lip with an attached applicator. Once in proper position, the user simply pulls the applicator away. When in place the lip enhancer stretches the inner lip tissue, causing more of the lip to be exposed externally, thus making the lip appear noticeably larger. Users may talk, eat, and drink while using the lip enhancer.

DETAILED DESCRIPTION OF PREFERRED EMBODIMENTS

Figure 1:
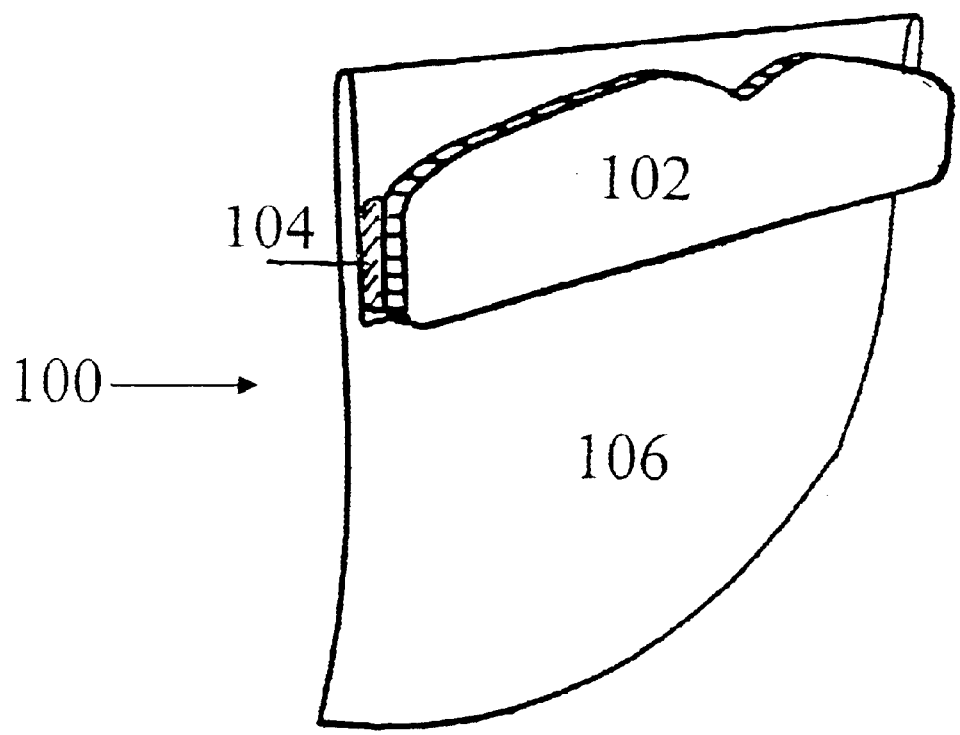
FIG. 1 is a perspective view of the lip enhancer apparatus, showing the relationship between the adhesive, the polymer, and the applicator.
Figure 2:
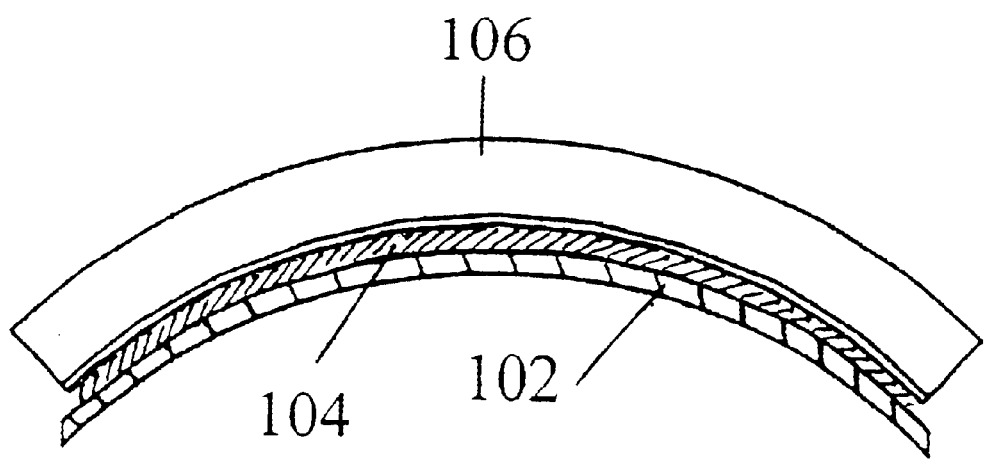
FIG. 2 is a top view of the lip enhancer apparatus.
Figure 3:
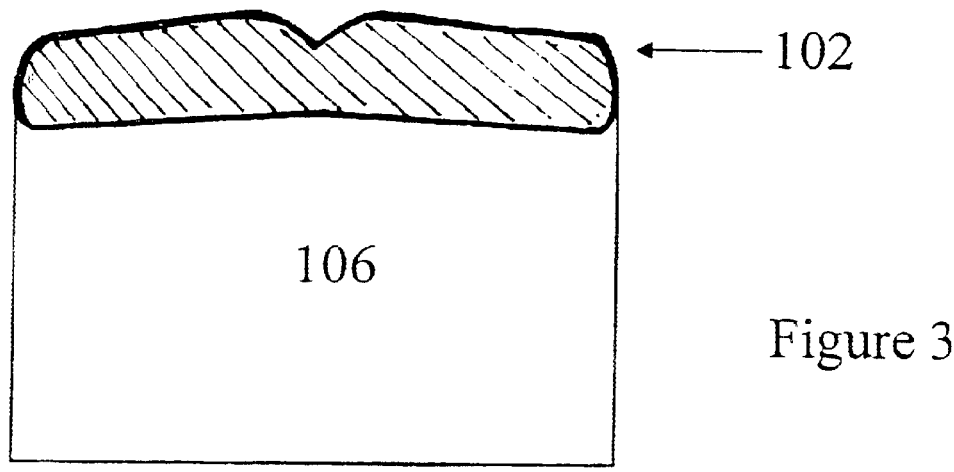
FIG. 3 is a front view of the lip enhancer apparatus.
Figure 4:
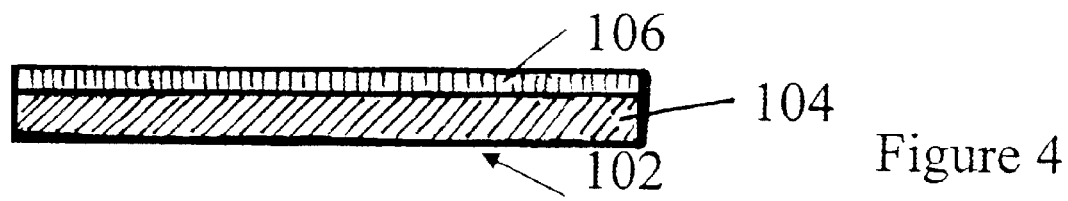
FIG. 4 is a top view of the lip enhancer apparatus.
Figure 5:
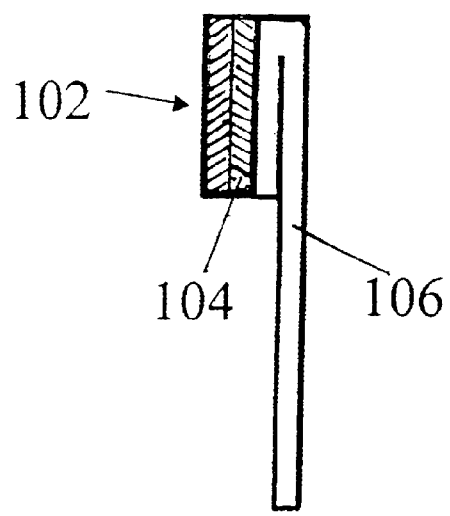
FIG. 5 is a side view of the lip enhancer apparatus.

Referring now to the figures, a preferred embodiment of the system is shown in FIG. 1. Lip Enhancer apparatus 100 is comprised of an adhesive 102, a polymer strip 104 and an applicator 106. The polymer strip 104 is positioned in between the applicator 106 and the adhesive 102.

The apparatus is extremely easy to use. The user pulls the lip away from the gums, stretching the mucosal area of the lip, and holds the applicator 106 to position the adhesive 102 and the polymer strip 104 to a desired position on the mucosal area of the lip. Once in position, the user presses firmly on the applicator 106 and the lip to bond the adhesive 102 to the mucosal area of the lip. After the adhesive has bonded, the applicator 106 is pulled away, leaving the adhesive 102 and the polymer strip 104 attached to the mucosal area of the lip. When in place the lip enhancer 100 maintains the "stretch" in the mucosal area of the lip, everting the lip, causing more of the lip to be exposed externally, thus making the lip appear noticeably larger.

The polymer strip 104, in a preferred embodiment, is either clear or flesh colored, so that it is not noticeable. The polymer strip should be non-reactive, and preferably should be pliable rather than rigid. A pliable material is preferable because users' mouths are a non-uniform shape. Additionally, the polymer strip should be relatively thin, with a preferred thickness between 1/64" and 1/16", length between 1" and 2½", and height of between 10–90% of the height of the average mucosal area of the lip. Alternatively, the polymer strip may come in a square size, larger than the size of the user's mucosal area, where the user can cut the polymer and adhesive to a size of the user's liking.

The adhesive 102, in a preferred embodiment, is a moisture-activated bioadhesive. A moisture-activated bioadhesive can be described as a material that, in the presence of aqueous fluid, forms adhesive interactions with biological substrates. Consequently, the adhesive remains "sticky" inside the mouth for a prolonged period. These materials are distinct from conventional pressure-sensitive adhesives, where adhesive bond failure occurs in the presence of aqueous fluid or very humid conditions. Moisture-activated bioadhesives will readily attach (and conform) to the inside of the lip. At the same time, however, when a moisture-activated bioadhesive is removed, it is painless and does not tear any tissue on the inside of the lip. The adhesive 102 is preferably the same size or smaller than the polymer strip 104, although it may be larger. In an alternative embodiment, the adhesive must pre-moistened to activate the adhesive before it is attached to the mucosal area of the lip.

The applicator 106, in a preferred embodiment, is a fairly rigid wrapper-type paper material, similar to the type of paper used on adhesive bandages, but thicker. Also preferably, the applicator is folded over. The significance of the folded over design is that when the applicator 106 is pulled away, the applicator simply peels away from the polymer strip 104. The bond of the adhesive 102 to the inside of the lip is much stronger than the bond between the polymer strip 104 and the applicator 106, so that when the applicator 106 is removed the adhesive 102 and polymer strip 104 do not move.

Although the present invention has thus been described in detail with regard to certain preferred embodiments, it should be apparent to those skilled in the art that various adaptations and modifications of the present invention may be accomplished without departing from the spirt and the scope of the invention. Accordingly, the present invention is not limited to the specific embodiments illustrated herein. Those skilled in the art will understand that the detailed description as set forth above is not intended to limit the breadth of the present invention, which is instead defined by the appended claims and their appropriately construed legal equivalents.

What is claimed is:

1. An apparatus for enlarging lips, comprising:
   an adhesive, between 10–90% the height of a mucosal area of a human lip, for adhering to the mucosal area of a human lip;
   a polymer strip attached to the adhesive, substantially the same size as the adhesive, for everting a portion of the human lip;
   an applicator attached to the polymer strip, wherein the applicator is used to position the adhesive and the polymer strip on the mucosal area of the human lip, wherein the applicator is thereafter removed.

2. The apparatus of claim 1, wherein the adhesive comprises a moisture-activated bioadhesive.

3. The apparatus of claim 1, wherein the polymer strip comprises a pliable, non-reactive polymer.

4. The apparatus of claim 1, wherein the applicator comprises semi-rigid slick paper material.

5. The apparatus of claim 4, wherein the applicator is folded above a position of the polymer strip, wherein removal of the applicator comprises the applicator peeling away from the polymer strip.

6. A method for enlarging lips, comprising:
   stretching a mucosal area of a human lip in order to evert a portion of the lip;
   adhering a polymer strip to the stretched mucosal area, using an adhesive, to maintain the lip in an everted position.

7. The method of claim 6, wherein adhering a polymer strip includes:
   positioning an adhesive and a polymer strip on the stretched mucosal area of the lip with an applicator, wherein the applicator is attached to the polymer strip and the polymer strip is attached to the adhesive;
   adhering the adhesive to the stretched mucosal area; and
   removing the applicator from the polymer strip, leaving the polymer strip and the adhesive attached to the stretched mucosal area, wherein the adhesive and the polymer strip maintain the stretch on the mucosal area of the lip.

8. The method of claim 6, wherein the adhesive comprises a moisture-activated bioadhesive.

9. The method of claim 6, wherein the polymer strip comprises a pliable, non-reactive polymer.

10. The method of claim 7, wherein the applicator comprises a semi-rigid slick paper material.

11. The method of claim 10, wherein the applicator is folded above a position of the polymer strip, wherein removal of the applicator comprises the applicator peeling away from the polymer strip.

12. An apparatus for enlarging lips, comprising:
    a polymer strip sized and configured to fit within a mucosal area of a human lip and evert a portion of the lip when adhered to the mucosal area; and
    an adhesive for adhering the polymer strip to the mucosal area of the lip.

13. The apparatus of claim 12, wherein the adhesive comprises a moisture-activated bioadhesive.

14. The apparatus of claim 12, wherein the polymer strip comprises a pliable, non-reactive polymer.

15. The apparatus of claim 12, wherein removal of the adhesive from the mucosal area of a human lip does not tear the mucosal area of the lip.

* * * * *